United States Patent [19]

Campbell et al.

[11] Patent Number: 4,997,990

[45] Date of Patent: Mar. 5, 1991

[54] PROCESS AND COMPOSITION FOR STABILIZATION OF AR-BROMINATED STYRENIC MONOMER

[75] Inventors: Stephen M. Campbell, New England, W. Va.; John C. Wozny, Coolville, Ohio

[73] Assignee: General Electric Company, Parkersburg, W. Va.

[21] Appl. No.: 327,553

[22] Filed: Mar. 23, 1989

[51] Int. Cl.$^5$ .............................................. C07C 7/20
[52] U.S. Cl. ......................................... 585/2; 203/9; 252/182.29; 252/385; 252/397; 585/24; 585/833; 585/952
[58] Field of Search .................. 252/385, 397, 182.29; 203/8, 9; 585/8, 24, 832, 833, 952

[56] References Cited

U.S. PATENT DOCUMENTS

| | | | |
|---|---|---|---|
| 2,965,685 | 12/1960 | Campbell | 585/4 |
| 3,247,242 | 4/1966 | McGarvey | 585/4 |
| 3,248,440 | 4/1966 | Albert | 585/4 |
| 3,274,077 | 9/1966 | Hoffenberg | 585/4 |
| 3,287,430 | 11/1966 | Haines et al. | 585/4 |
| 3,341,487 | 9/1967 | Albert et al. | 585/4 |
| 4,161,495 | 7/1979 | Detz | 585/4 |
| 4,276,189 | 6/1981 | Jackisch | 585/4 |

FOREIGN PATENT DOCUMENTS 163428 6/1976 Czechoslovakia .
1230979 5/1971 United Kingdom .

OTHER PUBLICATIONS

Product Data Specification Sheets 1866 and S-226, Pennsalt Rubber Chemicals (1969, 1967).
Frank, R. L. and Adams, C. E., "The Relative Efficiency of Some Polymerization Inhibitors", *Journal of the American Chemical Society*, vol. 68, p. 908 (1946).
Cubbon, R. C. P, and Smith, J. D. B., "The Properties of Nuclear Brominated Styrenes I—The Synthesis and Polymerization of Dibromostyrene and Tribromostyrene", *Polymer*, vol. 10, No. 7, pp. 479–487 (1969).
Hammond, G. S., "The Decomposition of Benzoyl Peroxide in the Presence of Iodine. I. Aromatic Solvents", *Journal of the American Chemical Society*, vol. 72, (Oct. 1950), pp. 3737–3743.
Hammond, G. S. and Soffer, L. M., "The Decomposition of Benzoyl Peroxide in the Presence of Iodine. II. In Carbon Tetrachloride Solution", *Journal of the American Chemical Society*, vol. 72, (Oct. 1950), pp. 4711–4715.
Perret, A. and Perrot, K., *Helv. Chim. Acta*, vol. 28, (1945), pp. 558–575.
"The Oxidizing Action of Benzoyl Peroxide in the Presence of Iodine on Some Unsaturated Hydrocarbons", *Chemical Abstracts*, vol. 40, 1480.
Imoto, M. et al, "Polar Effects in Radical Polymerization of p–Substituted Styrenes", *Die Makromolekulare Chemie*, vol. 86, pp. 217–340 (1965).
Gordon, A. J. and Ford, R. A., "The Chemists Companion" (New York, Wiley–Interscience, 1972), p. 437.

*Primary Examiner*—Asok Pal
*Attorney, Agent, or Firm*—Lowe, Price, Leblanc, Becker & Shur

[57] ABSTRACT

A process for stabilizing vinyl monomers in general, and ar-brominated styrene polymer in particular, against polymerization by mixing a vinyl monomer such as an ar-brominated styrene monomer with a stabilizing amount of iodine composition to produce a stabilized monomer and novel stabilized compositions.

17 Claims, 2 Drawing Sheets

PROCESS AND COMPOSITION FOR STABILIZATION OF AR-BROMINATED STYRENIC MONOMER

SUMMARY OF THE INVENTION

This invention relates to polymerization retarders and inhibitors in general and to stabilizing agents for prevention of premature polymerization of vinyl monomers in general and ar-brominated styrene monomer in particular.

Vinyl aromatic monomers tend to polymerize spontaneously upon standing. During the manufacture, shipping, and storage of these compounds, inhibitors are normally added to prevent, or at least retard, polymerization until such time that these compounds are intentionally converted to polymers.

Many stabilizing agents for the prevention of premature polymerization of monomers in general have been reported in the literature. For example, Czechoslovakian Patent Document No. 163,428 (Konecny et al.) recites several compositions which are known to stabilize one or more vinyl aromatic monomers: sulfur, copper, silver, gold, activated carbon, triphenylarsine, ammonia, diazoaminobenzene, some diolefins, phenylacetylene, sym-trinitrobenzene, p-benzoquinone, acetaldehyde, aniline condensates, N,N'-dibutyl-o-phenylenediamine, N-butylp-aminophenol, 2,4,6-triphenylphenoxyl, pyrogallol, pyrocatechol, hydroquinone, alkyl-substituted pyrocatechols, dialkylhydroquinone, 2,4,6-dichloronitrophenol, halogen-ortho-nitrophenols, alkoxyhydroquinone, mono-, di-, and polysulfides of phenols and pyrocatechols, aromatic nitrocompounds, amines, thiols, oximes or hydrazones of quinone, phenothiazine, dialkylhydroxylamines, and nitro compounds. However, as also noted by Konecny et al., only a few of the known stabilizers are commercially employed, with benzoquinone, hydroquinone, and tert-butylpyrocatechol mentioned by name. The other stabilizers have various shortcomings including undesirable levels of toxicity, explosiveness, or insufficient stabilizing activity. Also, many of the above listed compounds are noted to be stabilizers in conjunction with only a limited group of monomers.

While dialkylhydroxylamine compounds such as diethylhydroxylamine (DEHA)-containing compositions have been described among a wide range of types of chemicals useful for stabilizing vinyl aromatic compounds, such as styrene, its use with brominated styrenes has not been addressed.

Only a few compositions have been described as useful for stabilizing ar-brominated styrenes such as dibromostyrene. In British Patent Document 1,230,979, dibromostyrene (DBS) is described as being stabilized by picric acid or by a mixture of picric acid with a quinone or phenol, such as hydroquinone, benzoquinone and t-butyl catechol. Unfortunately, picric acid has the undesirable characteristics of coloring monomers bright yellow and, when concentrated, being shock sensitive, i.e. highly explosive.

Also, U.S. Pat. No. 4,276,189 (Jackisch) describes a process for retarding polymerization of dibromostyrene by addition of a metal oxide, such as magnesium, calcium, or zinc oxide, with or without an additional stabilizing agent such as 4-tert-butylcatechol and most benzoquinones.

The use of iodine as an inhibitor for brominated styrenes is novel. Reference to iodine has been found concerning the elucidation of the mechanism of decomposition for benzoyl peroxide in various solvents. Iodine was added to minimize the undesired side reaction of radical attack on peroxide which is known to result in induced decomposition of benzoyl peroxide. Also, addition of aqueous potassium iodide solution to an unknown liquid has been used as a qualitative test for the detection of peroxides. Iodide is oxidized to iodine.

See e.g. G. S. Hammond, J. Am. Chem. Soc. 72, 3737 (1950), G. S. Hammond and L. M. Soffer, J. Am. Chem. Soc. 72, 4711, (1950), A. Perret and R. Perrot, Helv. Chim. Acta., 28, 558 (1945) and A. J. Gordon and R. A. Ford, "The Chemists' Companion", page 437, Wiley Interscience, (1972).

SUMMARY OF THE INVENTION

According to the present invention, a novel process for stabilizing vinyl monomer against polymerization is described in which a vinyl monomer such as mono-, di-, or tri-bromostyrene or mixtures thereof are contacted or admixed with a stabilizing or polymerization inhibiting amount of an iodine composition, such as elemental iodine, to produce a stabilized monomer. Surprisingly, amounts of elemental iodine as low as 500 ppm will stabilize ar-brominated styrene monomer for a period of 88 hours at temperatures at or below 50° C.

The inventive process produces stabilized vinyl monomer compositions such as a stabilized ar-brominated styrene monomer composition which resists premature polymerization and may be stored, handled, transported, and subsequently polymerized with a greater deal of control, safety and economy relative to unstabilized monomer. In particular, dibromostyrene monomer may be maintained for a longer period of time without undesirable polymerization.

DETAILED DESCRIPTION OF THE INVENTION

Figure 1:
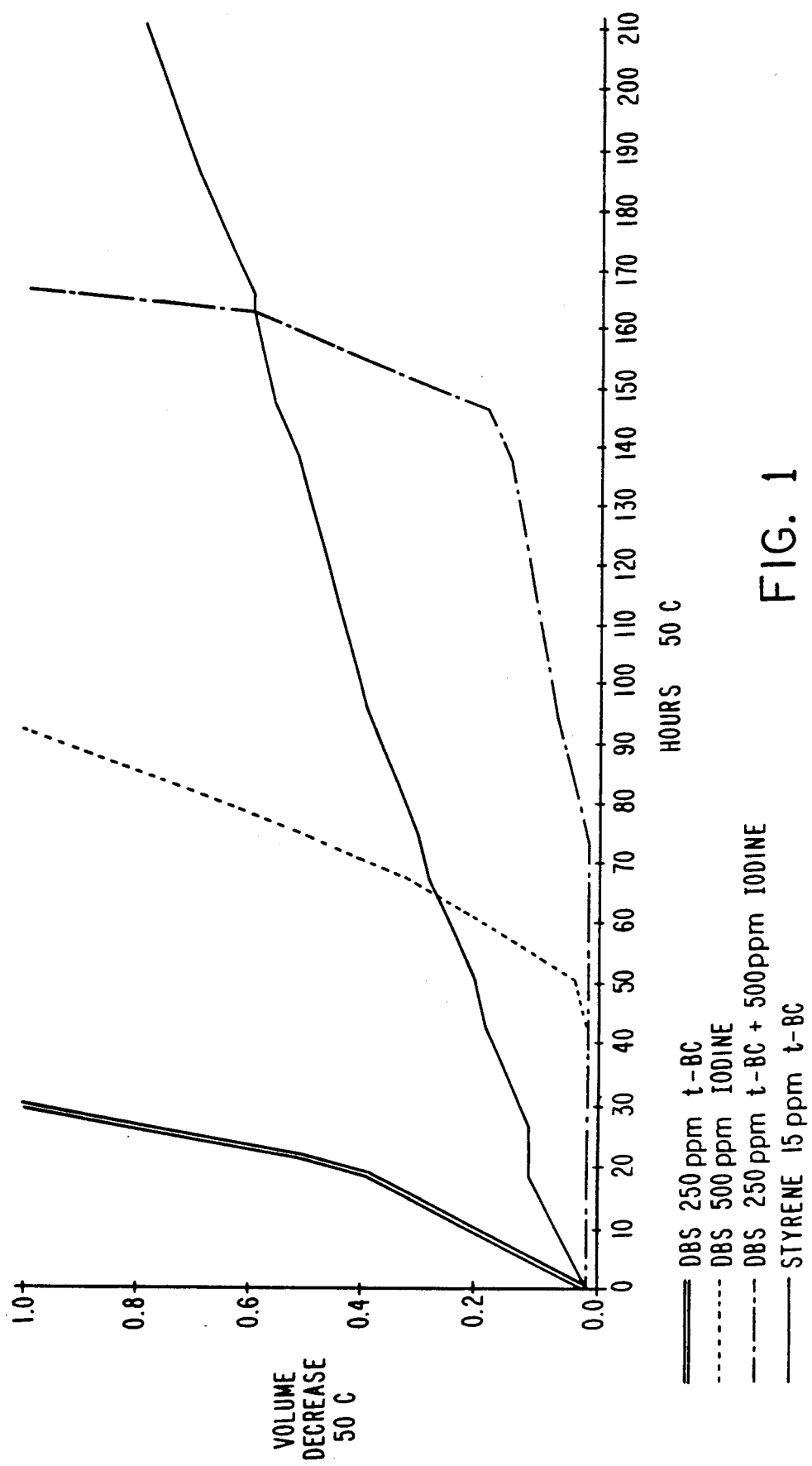
FIG. 1 is a graphical representation of Table 3 comparing percent volume decrease of monomer (which indicates relative degree of polymerization) versus time for stabilized styrene and dibromostyrene monomer.

The present invention is useful in the stabilization of vinyl monomers, including vinyl aromatic monomers, such as ar-brominated styrene monomers, against premature polymerization. It is desirable to prevent or retard the rate of polymerization in order to ship or store monomer until required for use. Brominated styrenes such as dibromostyrene have been proposed as a flame retardant monomer for use in making flame retardant polymers, such as acrylonitrile-butadiene-styrene graft polymers (ABS).

Use of iodine compositions as stabilizers is particularly advantageous for ar-brominated styrene monomers. In spite of the large number of inhibitors that have been discovered for vinyl aromatic compounds, few would be expected to find applicability with dibromostyrene.

Brominated styrenes have shown a markedly greater tendency to polymerize than styrene monomer alone. Table 1 shows polymerization constants ($K_p$) and termination constants ($K_t$) for styrene and mono-substituted halostyrene monomers in dimethylacetamide at about 30 degees C. as published by Imoto et al., *Makromol. Chem.*, (1965), 86, 217.

TABLE 1

| Monomer | $K_p$ l/mole sec | $K_t \times 10^6$ l/mole sec |
| --- | --- | --- |
| Styrene | 106 | 108 |
| Styrene p-F | 112 | 127 |
| Styrene p-Cl | 150 | 77 |
| Styrene p-Br | 186 | 46 |

As shown in Table 1, the rates of polymerization ($K_p$) for styrene and substituted styrene monomers indicates that halogenated styrenes are significantly more reactive than unsubstituted styrene and therefore more difficult to stabilize against premature polymerization. Also, since the termination rate ($K_t$) for an active bromostyrene radical is lower than that for styrene or its p-F or p-Cl analogs, the brominated styrenes are especially difficult to stabilize. With a lower termination rate ($K_t$) a greater amount of polymer is formed for each active free radical than for monomers having high $K_t$ values. Cubbon and Smith in their article entitled, "The Properties of Nuclear Brominated Styrenes I—The Synthesis and Polymerization of Dibromostyrene and Tribromostyrene," Polymer, Vol. 10, no. 7 (1969) pp 479–487, (which article is hereby incorporated by reference) have shown in their FIG. 1 that the polymerization rate of dibromostyrene is more than ten times greater than styrene.

It is also noted that dibromostyrene formed by conventional processes may be a mixture of mono-, di-, and tri-bromostyrenes. Tribromostyrene has an even greater tendency to polymerize than the highly reactive dibromostyrenes. Cubbon and Smith, supra, further state the order of rates of thermal polymerization to be: 2,4,5-tribromostyrene>2,4- and 3,4 dibromostyrene> >styrene.

Many known stabilizers for styrene are ineffective or poor polymerization inhibitors for substituted styrenes. Also, many free radical stabilizers are effective at high temperatures, but do not follow a first order stability relationship to room temperature. Therefore, the stabilizing capacity of inhibitors should be determined at or near the actual conditions contemplated.

Suitable iodine compositions for use as stabilizers or polymerization inhibitors in the present invention to include elemental iodine, inherhalogen compounds containing iodine, iodine compounds, such as organic iodides, and iodine salts such as sodium iodide. Advantageously, solid crystals of elemental iodine may be employed. Another advantage of the present invention is that addition of iodine may be used as a visual or colormetric indication of stabilizing activity. Addition of elemental iodine to dibromostyrene produces a reddish solution whose color intensity decreases and turns yellowish as the iodine reacts within the solution. Therefore an observer may obtain a visual indication of the stability of the solution against premature polymerization by a color comparison of a test sample to a sample of known stability.

Beneficially, iodine compositions according to the present invention may be utilized with other stabilizing or polymerization inhibiting agents including the stabilizers listed by Konecny and especially including hindered phenols like t-butylcatechol and quinones.

Following are examples given to illustrate the process and compositions of the invention. Evidence of polymerization was followed by the dilatometric method. All examples were conducted at 50° C. and at atmospheric pressure. The experimental methodology was as follows:

Monomer samples were prepared for testing by introducing a precisely known weight of a test inhibitor into a clean 9 inch Kimble 2075C cream test bottle. (A cream test bottle consists of a large flat bottomed bulb which tapers into a long narrow neck; the neck is calibrated in arbitrary units from 0 to 50.) A known weight of monomer was then added in portions with intermittent mixing to yield the indicated concentration of the test substance in the monomer. Each bottle was stoppered and mixing was completed by inverting the bottle 25 times. (The volumes were precalculated to yield a level of about 25 on the scale.) The stopper was removed and the bottle was loosely covered with aluminum foil to eliminate evaporation. The above procedure, and use of a long narrow necked bottle, acts to minimize air exposure. Minimum air exposure is desirable as an experimental condition because it simulates reasonable expected static storage conditions for bulk handling of this monomer. The bottles were immersed into a constant temperature bath at $50.00° +/- 0.02°$ C. and allowed to equilibrate. After equilibration, the volume was readjusted to exactly 25.0 on the bottle scale. The volume change was recorded versus time to monitor any conversion to polymer. A 5 unit change on the bottle scale was determined to be equal to a 1% change in total volume at midscale. A stabilizing amount is defined as sufficient added inhibitor to stop or retard polymerization for a time exceeding that observed for a monomer without added inhibitor. Excessive polymerization is defined as polymerization producing a one percent or greater decrease in total volume.

The styrene used in the examples was commercially available and used as received from Cosden Chemical Company. The dibromostyrene was obtained as an experimental monomer mixture of monobromostyrene, dibromostyrene, and tribromostyrene from Great Lakes Chemicals under the name of "Dibromostyrene" and from Ethyl Corporation under the name of "Satex RB-25". No difference between the two monomers was observed with respect to stabilizer response. N,N-diethylhydroxylamine was purchased from Aldrich Chemical Company at 97% purity under the product designation of D 9720-7. The iodine composition was commercially available solid crystalline elemental iodine.

Test results are shown in Tables 2 and 3 for ease of comparison. Referring now to Table 2, Examples 1, 2, 3 and 9 are comparative Examples and Examples 4, 5, 6, 7, 8 and 10 are of the present invention.

TABLE 2

DBS MONOMER STABILITY

| Ex. No. | Sample | TBC ppm | IODINE ppm | Time in Hours to Reach The Indicated Volume Decrease @ 50° | | |
|---|---|---|---|---|---|---|
| | | | | 0.2% | 0.5% | 1.0% |
| 1 | Styrene | 15 | 0 | 57 | 120 | 145 |
| 2 | DBS | 0 | 0 | 1.5 | 3 | 7 |
| 3 | DBS | 250 | 0 | 10 | 21 | 27 |
| 4 | DBS | 0 | 500 | 62 | 76 | 88 |
| 5 | DBS | 250 | 100 | 31 | 41 | 54 |
| 6 | DBS | 250 | 250 | 80 | 92 | 104 |
| 7 | DBS | 250 | 500 | 147 | 154 | 165 |
| 8 | DBS with 250 ppm DEHA | 250 | 100 | 44 | 64 | 87 |
| 9 | DBS (*) | 250 | 0 | >.2 | 0.2 | 0.4 |
| 10 | DBS (*) | 250 | 500 | 6 | — | <18 |

(*) Polymerization intentionally begun with initiator.

Examples 1 and 3 (not of the Invention)

Examples 1 and 3 in Table 2 show that dibromostyrene stabilized with 250 ppm t-butyl catechol (t-BC) is less than one fifth as stable as the commercial styrene sample containing only 15 ppm t-butyl catechol as measured by a 1% volume decrease. While t-BC added to dibromostyrene will provide some degree of stabilization, it is not comparable to the level of stabilization afforded to styrene by t-BC.

Sample 4

Example 4 in Table 2 shows that dibromostyrene stabilized with 500 ppm of iodine is three times as stable as dibromostyrene with 250 ppm t-BC when compared at the 1% polymer level. At the 0.2% polymer level the example 4 dibromostyrene monomer exhibited six times the stability of example 3. This greater stabilization by iodine to very low polymer formation is important because even small amounts of polymer in the monomer render the dibromostyrene less suitable for use in subsequent processes. Also, at the 0.2% polymer level the stabilization time for dibromostyrene containing 500 ppm Iodine (Example 4) exceeds the stabilization time for the commercial styrene (Example 1) sample.

Examples 5, 6, and 7

Figure 2:
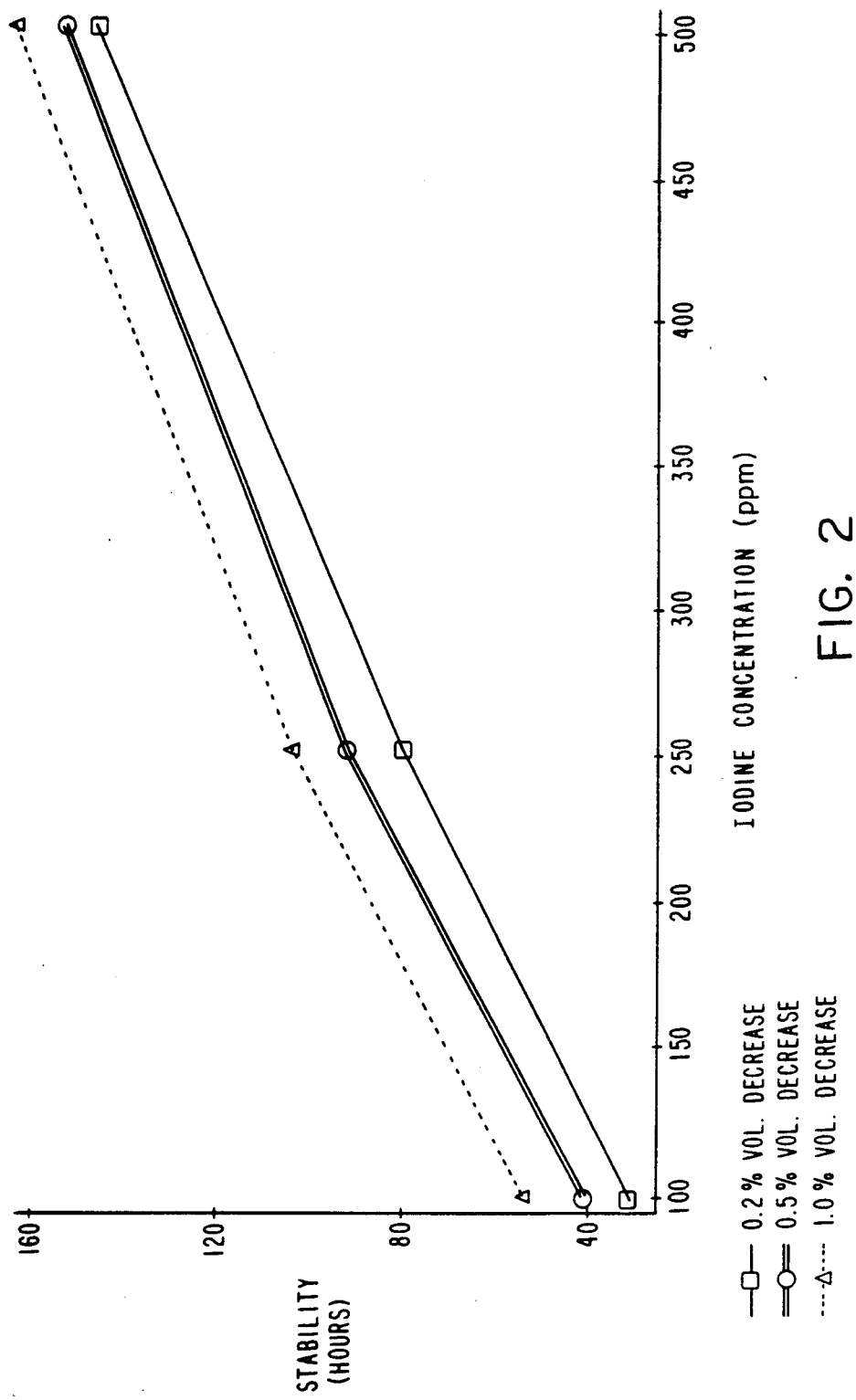
FIG. 2 illustrates the effect of iodine on the stability against premature polymerization of dibromostyrene, and shows that it is a linear function of the iodine concentration in the monomer.

Comparison among Examples 5, 6, and 7 of the invention shows that the stability of dibromostyrene is a function of the iodine concentration. FIG. 2 illustrates that stability is proportional to the iodine concentration. Examples 5, 6, and 7 show that there is also a synergistic interaction between iodine and t-BC in the stabilization of dibromostyrene. Comparison of example 7 with example 3 and 4 shows an unexpected stabilizing effect of the combination of iodine and t-BC. The stabilization time of Example 7 exceeds the sum of the stabilizing times of Examples 3 and 4 by 150% to 200%.

Example 8

Comparison of Example 5 with Example 8 shows that the addition of DEHA to the iodine inhibitor with t-BC further stabilizes the dibromostyrene against premature polymerization.

Examples 9-10

Examples 9 and 10 demonstrate the ability to initiate polymerization when desired by addition of a polymerization initiator. DBS containing 500 ppm elemental iodine and 250 ppm t-BC began rapidly polymerizing in less than 18.5 hours when initiated in bulk with a low radical flux polymerization initiator such as 0.5% by weight of a commercially available initiator sold under the trade name "VAZO 52" by E.I. DuPont de Nemours Co. at 50° C. DBS containing only the t-BC exhibited rapid polymerization onset after 0.4 hours under the same conditions. In both cases polymerization continued to form a glassy solid homopolymer.

Referring now to Table 3, the percent volume decrease at 50° C. for Examples 1, 3, 4, and 7 from Table 2 is expressed in more detail with periodic determinations over time. This data ia graphically presented in FIG. 1.

Example 2 (Control—Not of the Invention)

As shown by the data in Example 2 of Table 2, dibromostyrene monomer, without any stabilizing agent, quickly polymerizes until a one percent drop in volume occurs after only seven hours. Thus, without inhibitor the original monomer quickly converts to polymer necessitating costly removal steps and rendering that portion of the monomer unsuitable for its intended purpose. The stability against premature polymerization of unstabilized dibromostyrene (DBS) may vary from one to several hours at 50° C. when tested with minimum exposure to oxygen from the air.

TABLE 3

% VOLUME DECREASE AT 50° C.

| | Example | | | |
|---|---|---|---|---|
| Monomer Inhibitor | 1 Styrene 10 ppm t-BC | 3 DBS 250 t-BC | 4 DBS 500 Iodine | 7 DBS 500 ppm Iodine + 250 ppm t-BC |
| 0 hr. | 0 | 0 | 0 | 0 |
| 18 hr. | .1 | .38 | 0 | 0 |
| 21 hr. | .1 | .5 | 0 | 0 |
| 26 hr. | .1 | .8 | 0 | 0 |
| 42 hr. | .18 | 1.9 | 0 | 0 |
| 50 hr. | .2 | 2.4 | .02 | 0 |
| 66 hr. | .28 | 3.24 | .3 | 0 |
| 74 hr. | .3 | 3.6 | .5 | 0 |
| 97 hr. | .4 | 4.6 | 1.18 | .06 |
| 138 hr. | .52 | | | .14 |
| 146 hr. | .56 | | | .18 |
| 162 hr. | .6 | | | .6 |
| 165 hr. | .6 | | 3.7 | 1.0 |
| 170 hr. | .62 | | | 1.4 |
| 185 hr. | .7 | | | 2.2 |
| 210 hr. | .8 | | | 3.34 |

Examples 4 and 7 in Table 3 show that the induction period before undesirable or excessive polymerization (1% volume decrease) for 500 ppm elemental iodine in dibromostyrene with or without 250 ppm t-BC was 165 and 88 hours respectively. FIG. 1 graphically represents the data of Table 3 by comparing the percent volume decrease against time for Examples 1, 3, 4, and 7. Interestingly, addition of iodine greatly reduces initial premature polymerization relative to the use of t-BC alone. It is believed without wishing to be bound by that belief that iodine inhibits quantitatively until depleted, after which a rapid polymerization may occur. This is in contrast to the use of other stabilizing agents such as t-BC and diethylhydroxylamine in which use polymerization proceeds slowly until depletion of the stabilizer.

The stabilized solution of brominated styrenes according to the present invention is initially red and slowly fades to dark yellow as the iodine stabilizer is consumed, and then to the pale yellow of the monomer whereupon polymerization occurs.

The high reactivity of dibromostyrene toward polymerization tends to limit the storage stability and handling latitude of this monomer. Surprisingly, stabilization of the dibromostyrene with an iodine composition such as elemental iodine shows that dibromostyrene may be stabilized with a long induction period showing virtually no polymerization. Either iodine alone or the combination of iodine with t-BC is clearly superior to the use of t-BC alone and addition of other stabilizers such as DEHA may also be usefully employed. Also, an iodine composition inhibitor has the added advantage that it can be readily overcome by free radical initiators when the iodine is used at levels which provide adequate storage stability in dibromostyrene. Sufficient storage stability can be achieved in a vinyl monomer such as DBS at iodine concentrations below the level where polymerizability is adversely affected. Other iodine compositions are believed to be suitable, especially iodine salts.

The above examples show that useful novel iodine containing stabilized vinyl monomer compositions may be formed according to the present invention. In particular, stabilized vinyl aromatic monomers such as dibromostyrene or mixtures of ar-brominated styrenes may be formed.

The above examples serve only to illustrate the invention and its advantages and should not be interpreted as limiting since further modifications of the disclosed invention will be apparent to those skilled in the art. All such modifications are deemed to be within the scope of the invention as defined by the following claims.

What is claimed is:

1. A process for stabilizing vinyl monomer against polymerization comprising the steps of: contacting vinyl monomer with a stabilizing amount of an iodine composition to produce a stabilized monomer.

2. A process as defined in claim 1 wherein said vinyl monomer is a vinyl aromatic monomer.

3. A process as defined in claim 1 wherein said vinyl monomer is ar-brominated styrene monomer.

4. A process as defined in claim 3 wherein said ar-brominated styrene comprises dibromostyrene monomer.

5. A process as defined in claim 1 wherein said stabilizing amount is from about 2 ppm to about 50,000 ppm.

6. A process as defined in claim 1 wherein said iodine composition is elemental iodine.

7. A process as defined in claim 3 wherein ar-brominated styrene monomer comprises a mixture of ar-brominated styrenes forming a composition having from about 0.8 to about 3.2 bromines per aromatic ring.

8. A process as defined in claim 1 further comprising a stabilizing amount of t-butylcatechol.

9. A process for inhibiting rapid polymerization of ar-brominated styrene comprising admixing a polymerization inhibiting amount of an iodine composition with ar-brominated styrene monomer to produce a stable monomer.

10. A process as defined in claim 9 wherein said iodine composition comprises elemental iodine.

11. A process as defined in claim 9, wherein said inhibiting amount is sufficient to maintain monomer at a level of 99% of its original volume for a period of at least 50 hours at temperatures at or below 50° C.

12. A halogenated vinyl aromatic monomer composition comprising an ar-brominated styrene monomer admixed with an iodine composition sufficient to inhibit polymerization.

13. A composition as defined in claim 12 wherein said iodine composition is present in an amount between about 2 ppm to about 10,000 ppm by weight.

14. A composition as defined in claim 12 wherein said ar-brominated styrene monomer comprises dibromostyrenes.

15. A composition as defined in claim 12 wherein said ar-brominated styrene monomer comprises a mixture of mono-, di-, and tri-bromostyrene.

16. A process as defined in claim 1 further comprising a stabilizing amount of N,N-dialkylhydroxylamine.

17. A composition as defined in claim 12 wherein said halogenated vinyl aromatic monomer and iodine composition are additionally admixed with a hindered phenol, t-butyl catechol, a catechol, a quinone, hydroquinone, diethylhydroxylamine, or mixtures thereof.

* * * * *